United States Patent [19]

Rosini et al.

[11] Patent Number: 5,466,682
[45] Date of Patent: Nov. 14, 1995

[54] ACYLAMINO-ALKYLIDEN-HYDROXY-BISPHOSPHONIC ACIDS ESTERS AND SALTS THEREOF, WHEREIN THE ACYL GROUP IS DERIVED FROM AN ACID HAVING ANTIINFLAMMATORY ACTIVITY

[75] Inventors: Sergio Rosini; Maurizio Mian, both of Pisa, Italy

[73] Assignee: Istituto Gentili S.p.A., Pisa, Italy

[21] Appl. No.: 94,160

[22] PCT Filed: Jan. 20, 1992

[86] PCT No.: PCT/EP92/00102

§ 371 Date: Jul. 26, 1993

§ 102(e) Date: Jul. 26, 1993

[87] PCT Pub. No.: WO92/13864

PCT Pub. Date: Aug. 20, 1992

[30] Foreign Application Priority Data

Feb. 1, 1991 [IT] Italy ................... MI91A0254

[51] Int. Cl.[6] .................... A61K 31/66; A61K 37/02; C07F 9/572; C07F 9/38; C07F 9/40; C07F 9/65
[52] U.S. Cl. .................... 514/76; 514/86; 514/108; 514/119; 514/129; 562/12; 562/13; 548/113
[58] Field of Search .................... 562/13, 12; 514/108, 514/76, 119, 86, 129; 548/113

[56] References Cited

U.S. PATENT DOCUMENTS

| | | | |
|---|---|---|---|
| 4,029,697 | 6/1977 | Krueger et al. | 562/13 |
| 4,666,895 | 5/1987 | Bosies et al. | 514/108 |
| 4,857,513 | 8/1989 | Oku et al. | 514/76 |
| 4,876,248 | 10/1989 | Breliere et al. | 514/108 |
| 4,927,814 | 5/1990 | Gall et al. | 514/108 |
| 5,036,058 | 7/1991 | Jaeggi | 514/86 |
| 5,159,108 | 10/1992 | Kieczykowski | 562/13 |

FOREIGN PATENT DOCUMENTS

| | | | |
|---|---|---|---|
| 0084822 | 8/1983 | European Pat. Off. | 562/13 |
| 0197478 | 10/1986 | European Pat. Off. | 562/13 |
| 0243173 | 10/1987 | European Pat. Off. | 562/13 |
| 2651904 | 5/1978 | Germany | 562/13 |
| 2-104593 | 4/1990 | Japan | 562/13 |

*Primary Examiner*—Floyd D. Higel
*Attorney, Agent, or Firm*—Bucknam and Archer

[57] ABSTRACT

Compounds of formula (I)

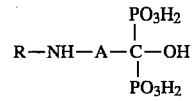

in which A is $(CH_2)_n$ in which n is 1–10, preferably 3 or 5, and R is the acyl group from a known anti-inflammatory agent, exhibit high anti-inflammatory activity. The mechanism of action is novel because they do not release the anti-inflammatory agent in the body but exhibit an activity superior to the activity of the known anti-inflammatory agent. The compounds are also active in combating bone calcium loss.

6 Claims, No Drawings

ACYLAMINO-ALKYLIDEN-HYDROXY-BISPHOSPHONIC ACIDS ESTERS AND SALTS THEREOF, WHEREIN THE ACYL GROUP IS DERIVED FROM AN ACID HAVING ANTIINFLAMMATORY ACTIVITY

This application is A371 of EP 92/00102 filed Jan. 20, 1992.

The present invention relates to compounds of general formula (I)

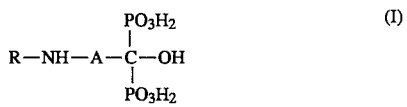

wherein

A is a —$(CH_2)$—$_n$ group with n comprised between 1 and 10;

R is an acyl residue from a known anti-inflammatory compound belonging in the class of salicylic, arylacetic, arylpropionic, anthranilic, 4,5-dihydroxy- or 4,5,8-trihydroxy-9,10-dihydro-9,10-dioxo-2-anthracenecarboxylic, nicotinic acids.

Examples of known anti-inflammatory acids, the acyl residues of which form the R group, as defined in formula (I], are reported hereinbelow:

salicylic acids: salicylic acid, acetylsalicylic acid, 5-aminosalicylic acid, diflunisal, fendosal;

arylacetic acids: acemetacin, alclofenac, amfenac, benzadac, bufexamac, bumadizone, cinmetacin, clidanac, clometacin, clopirac, diclofenac, etodolac, fenclofenac, indobufen, indometacin, methiazinic acid, sulindac, tolmetin, zomepirac;

propionic acids: alminoprofen, benoxaprofen, bucloxic acid, carprofen, flurbiprofen, ibuprofen, ketoprofen, loxoprofen, naproxen, oxaprozin, protizinic acid, pineprofen, pirprofen, pranoprofen, suprofen, thiaprofenic acid;

anthranilic acids: flufenamic acid, meclofenamic acid, mefenamic acid, niflumic acid, lobenzarit, tolfenamic acid;

4,5-dihydroxy- or 4,5,8-trihydroxy-9,10-dihydro-9,10-dioxo-2-anthracenecarboxylic acids: diacerhein, thiorhein.

Particularly preferred are the compounds of formula (I) wherein R is 2-acetoxybenzoyl, the residues from diflunisal, ibufenac, ibuprofen, naproxen, indometacin, diacerhein.

Most preferred compounds are those in which n is 3 or 5.

In case the residue R contains one or more chiral carbon atoms, the invention comprises the single enantiomers and the mixtures of racemates and of diastereoisomers thereof.

The invention also relates to the diphosphonic acid salts, the esters of both the phosphonic groups and the hydroxy group, with the proviso that they are pharmaceutically acceptable.

The compounds of formula (I) are prepared by the condensation of known anti-inflammatory compounds with known ω-aminoalkylene-1-hydroxy-1,1-diphosphonic acid derivatives already used in therapy due to their inhibiting action on bone resorption and antiurolithiasic action.

ω-Aminoalkylene-1-hydroxy-1,1-diphosphonic acids are described in Italian Patent Applications N. ITA230503 and ITA22295A8 and in German Patent Applications N. DE-OS 2,534,391 and DE-OS 3,540,150.

Alkyl-1-hydroxy-1,1-diphosphonic acid derivatives condensed with anti-inflammatory residues through a C—C bond are known from EP-A-84822.

The compounds of the invention, on the contrary, are characterized by an amido bond between the amino group of the ω-aminoalkylenehydroxydiphosphonic acid and the carboxy group of the anti-inflammatory compound.

Contrary to what could be assumed, the pharmacological properties of the compounds of formula (I) are not those typical of "pro-drugs" which can release "in vivo" the two components which independently carry on their therapeutical activities.

In fact, it has surprisingly been found that compounds (I) have a far higher anti-inflammatory activity than the activity which could be assigned to the "in vivo" release of a known RCOOH pharmacologically active acid. This is even more surprising because the aminoalkylhydroxydiphosphonic component is completely devoid of anti-inflammatory activity.

Compounds of formula (I) are prepared by reacting a compound of formula (II)

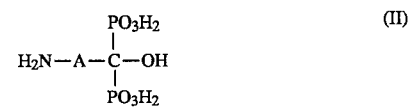

wherein A has the above mentioned meaning, with a compound of formula RCOOH, wherein R is as defined above, or with a reactive derivative thereof (chloride, anhydride, imidazolide etc.).

The reaction is preferably carried out in an aqueous medium in the presence of alkali, using a reactive derivative of the carboxy group of the R molecule, such as the acid chloride.

The advantageous properties of the compounds of the invention make them useful in the therapy of muscle-skeletal disorders.

Therefore, the compounds of the invention will be used for the preparation of pharmaceutical compositions in admixture with suitable excipients and/or other drugs which can adjuvate the therapeutic action.

Examples of said pharmaceutical compositions comprise both solid and liquid oral formulations, optionally in sustained-release or gastro-resistant forms, injectable formulations, optionally in depot forms, suppositories and topical forms.

The posology will be determined according to the pathology and patient's conditions (age, sex, weight) and the clinician's prescriptions. Dosage forms could be unit forms containing 2 to 500 mg of the active ingredient per unit dose.

The following examples further illustrate the invention.

EXAMPLE 1

[4-(2-Acetoxybenzoyl)-amino-1-hydroxybutylidene]-diphosphonic acid 3.18 g (9.8 mmoles) of sodium trihydrogen 4-amino-1-hydroxybutylidenediphosphonate trihydrate are added in 30 ml of water to 1.8 g (45 mmoles) of sodium hydroxide, 100 mg of p-dimethylaminopyridine and 200 mg of tetrahexylammonium iodide. The resulting solution is cooled to 0° C., and added with 2.03 g (10.2 mmoles) of 2-acetoxybenzoic acid chloride dissolved in 10 ml of diethyl ether. The reaction mixture is stirred for 2 hours at room temperature, then it is extracted with ethyl ether and the aqueous solution is acidified with concentrated HCl under stirring, with cooling. [4-(2-Hydroxybenzoyl)-amino-1-hydroxybutylidene]-diphosphonic acid precipitates, which is filtered, washed and dried at 70° C. and transformed into the title product by means of acetylation with acetic anhydride.

M.P. (dec.)>150° C.

| E.A. for $C_{13}H_{19}NO_{10}P_2$ | | |
|---|---|---|
| | theoretical % | found % |
| C | 37.96 | 38.04 |
| H | 4.65 | 4.69 |
| N | 3.40 | 3.45 |

I.R. and 1H N.M.R. in conformity.

EXAMPLE 2

[6-(2-Acetoxybenzoyl)-amino-1-hydroxyhexylidene]-diphosphonic acid

The procedure of example 1 is followed, but using 3.4 5 g (9.8 mmoles) of sodium trihydrogen 6-amino-1-hydroxyhexylidenediphosphonate trihydrate. [6-(2-Hydroxybenzoyl)-amino-1-hydroxyhexylidene]-diphosphonic acid precipitates. The procedure of example 1 is repeated, to obtain the title product, having the following characteristics:

M.P. (dec.)>150 ° C.

| E.A. for $C_{15}H_{23}NO_{10}P_2$ | | |
|---|---|---|
| | theoretical % | found % |
| C | 41.00 | 40.94 |
| H | 5.27 | 5.23 |
| N | 3.18 | 3.24 |

I.R. and 1H N.M.R. in conformity.

EXAMPLE 3

[4-[5-(2,4-Difluorophenyl)-2-hydroxybenzoyl]-amino-1-hydroxybutylidene]-diphosphonic acid The procedure of example 1 is repeated, using 3.18 g (10.2 mmoles) of 5-(2,4-difluorophenyl)-2-acetoxybenzoic acid chloride.

After acidification with concentrated HCl, the title product precipitates, having the following characteristics:

M.P. (dec)>150° C.

| E.A. for $C_{17}H_{19}F_2NO_9P_2$ | | |
|---|---|---|
| | theoretical % | found % |
| C | 42.41 | 42.36 |
| H | 3.97 | 3.94 |
| N | 2.90 | 2.98 |

I.R. and 1H N.M.R. in conformity.

Analogously to the above examples the following compounds have been prepared:

EXAMPLE 4

[6-[5-(2,4-Difluorophenyl)-2-hydroxybenzoyl]-amino-1-hydroxyhexylidene]-diphosphonic acid M.P. (dec)>150° C.

| E.A. for $C_{19}H_{23}F_2NO_9P_2$ | | |
|---|---|---|
| | theoretical % | found % |
| C | 44.80 | 44.85 |
| H | 4.55 | 4.58 |
| N | 2.74 | 2.80 |

I.R. and 1H N.M.R. in conformity.

EXAMPLE 5

[4-(4-Isobutylphenyl)-acetylamino-1-hydroxybutylidene]-diphosphonic acid

M.P. (dec)>150° C.

| E.A. for $C_{16}H_{27}NO_8P_2$ | | |
|---|---|---|
| | theoretical % | found % |
| C | 45.38 | 45.44 |
| H | 6.42 | 6.47 |
| N | 3.30 | 3.36 |

I.R. and 1H N.M.R. in conformity.

EXAMPLE 6

[6-(4-Isobutylphenyl)-acetylamino-1-hydroxyhexylidene]-diphosphonic acid

M.P. (dec)>150° C.

| E.A. for $C_{18}H_{31}NO_8P_2$ | | |
|---|---|---|
| | theoretical % | found % |
| C | 47.88 | 47.93 |
| H | 6.12 | 6.14 |
| N | 3.10 | 3.18 |

EXAMPLE 7

[4-[2-(4-Isobutylphenyl)-propionyl]-amino-1-hydroxybutylidene]-diphosphonic acid M.P. (dec)>150° C.

| E.A. for $C_{17}H_{29}NO_8P_2$ | | |
|---|---|---|
| | theoretical % | found % |
| C | 46.67 | 46.61 |
| H | 6.68 | 6.65 |
| N | 3.20 | 3.27 |

I.R. and 1H N.M.R. in conformity.

EXAMPLE 8

[6-[2-(4-Isobutylphenyl)-propionyl]-amino-1-hydroxyhexylidene]-diphosphonic acid M.P. (dec)>150° C.

| E.A. for $C_{19}H_{33}NO_8P_2$ | | |
|---|---|---|
| | theoretical % | found % |
| C | 49.02 | 48.96 |
| H | 7.14 | 7.09 |
| N | 3.00 | 2.95 |

I.R. and 1N.M.R. in conformity.

EXAMPLE 9

[4-[2-(6-Methoxynaphthyl)-propionyl]-amino-1-hydroxybutylidene]]-diphosphonic acid M.P. (dec)>150° C.

| E.A. for $C_{18}H_{25}NO_9P_2$ | | |
|---|---|---|
| | theoretical % | found % |
| C | 46.85 | 46.80 |
| H | 5.46 | 5.47 |
| N | 3.03 | 3.00 |

I.R. and 1H N.M.R. in conformity.

EXAMPLE 10

[6-[2-(6-Methoxynaphthyl)-propionyl]-amino-1-hydroxyhexylidene]-diphosphonic acid M.P. (dec)>150° C.

| E.A. for $C_{20}H_{29}NO_9P_2$ | | |
|---|---|---|
| | theoretical % | found % |
| C | 49.07 | 49.02 |
| H | 5.97 | 5.96 |
| N | 2.86 | 2.90 |

EXAMPLE 11

[4-[1-(4-Chlorobenzoyl)-2-methyl-5-methoxy-2-indolyl]-acetyl-amino-1-hydroxybutylidene]-diphosphonic acid M.P. (dec) 150° C.

| E.A. for $C_{23}H_{27}ClN_2O_{10}P_2$ | | |
|---|---|---|
| | theoretical % | found % |
| C | 46.90 | 46.99 |
| H | 4.62 | 4.66 |
| N | 4.75 | 4.68 |

I.R. and 1H N.M.R. conformity.

EXAMPLE 12

[6-[1-(4-Chlorobenzoyl)-2-methyl-5-methoxy-2-indolyl]-acetyl-amino-1-hydroxyhexylidene]-diphosphonic acid M.P. (dec)>150° C.

| E.A. for $C_{25}H_{31}ClN_2O_{10}P_2$ | | |
|---|---|---|
| | theoretical % | found % |
| C | 48.66 | — |
| H | 5.06 | — |
| N | 4.53 | — |

I.R. and 1H N.M.R. in conformity.

EXAMPLE 13

Carrageenin Oedema in Rat

Used substances:
  Carrageenin (control –)
  Carrageenin+Ibuprofen (11 and 5.5 mg/kg)
  Carrageenin+compound of example 8 (Br-Ax) (25.0 and 12.5 mg/kg)
  Carrageenin+compound of example 7 (Br-Ab) (25.0 and 12.5 mg/kg)
Note: Ibuprofen doses are equimolar to the corresponding Br-Ab and Br-Ax doses.
Used animals:
  S.D. male rats weighing 160–180 g
Test groups:
  1) Control - (Carrageenin only)
  2) Ibuprofen 11.0 mg/kg
  3) Ibuprofen 5.5 mg/kg
  4) Br-Ab 25.0 mg/kg
  5) Br-Ab 12.5 mg/kg
  6) Br-Aex 25.0 mg/kg
  7) Br-Aex 12.5 mg/kg Each group consisted of 5 males, trying to obtain the most homogeneous total weight for each group. The animals were inoculated subcutaneously with the test solutions homogenized in 5% gum Arabic which had been sterilized by filtration with "Acrodisc" Gelman with 0.45 µl pores.

After 1 hour the animals were slightly anaesthetized with 0.1 ml of 1% carrageenin in sterile saline. Carrageenin was kept under stirring by means of a magnetic stirred, to make it as homogeneous as possible.

At the same time, the basal paw volumes were determined by means of a plethysmograph, so as to make possible to repeat the measurements in the most reliable way in the subsequent hours.

2 Hours after carrageenin inoculation, the measure of paw volumes was determined (2nd hour). Subsequently, said measurement was effected at the 4th and 6th hours from inoculation. After that, the % protection was calculated by means of the following formula:

$$\frac{\text{Increase in paw volume of the treated group}}{\text{Increase of paw volume in control group}} \times 100 = A$$

$100 - A = \%$ Protection

TABLE 1

| Product | % Protection 2nd hour | % Protection 4th hour | % Protection 6th hour |
|---|---|---|---|
| Ibuprofen (11.0 mg/kg) | 21% | 25% | 28% |
| Ibuprofen (5.5 mg/kg) | 18% | 3% | 4% |
| Br—Ab (25.0 mg/kg) | 68% | 57% | 38% |
| Br—Ab (12.5 mg/kg) | 31% | 28% | 30% |
| Br—Ax (25.0 mg/kg) | 42% | 21% | 56% |
| Br—Ax (12.5 mg/kg) | 41% | 36% | 48% |

The obtained results show that all of the compounds of the invention give a higher protection than Ibuprofen; moreover, pharmacological differences exist among the compounds of the invention due to the methylene portion length (A in general formula).

EXAMPLE 14

Male rats weighing about 200 mg are thyroparathyroidectomyzed under Nembutal anaesthesia. The animals are treated with thyroxine on alternate days during all the test. 7 Days after surgery, blood is withdrawn by means of intracardiac puncture and Ca is determined on plasma. The animals with a Ca plasma content higher than 2 mM are excluded from the test, the others are treated with the compounds under test and with retinoid which is administered subcutaneously for 3 consecutive days. 24 Hours after the last administration, animals are killed and blood is recovered to determine Ca again.

TABLE 2

EFFECT OF BR—AB AND BR—AX DERIVATIVES ON BONE CALCIUM LOSS INDUCED BY RETINOID IN RAT

| Compound | Plasmatic Ca increase after retinoid adm. (mmol/lt) | % inhibition |
|---|---|---|
| Controls | 1.11 ± 0.03 | — |
| AHBuBP | 0.29 ± 0.2 | 73.9 |
| BR—AB | 0.62 ± 0.03 | 44.1 |
| BR—AX | 0.75 ± 0.17 | 32.4 |

Note:
AHBuBP is 4-amino-1-hydroxybutylidene-1,1-diphosphonic acid.

We claim:

1. A compound of formula (I)

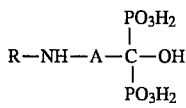

wherein A is a —$(CH_2)_n$— wherein n is between 1 and 10; R is an acyl radical from a known anti-inflammatory compound which is a member selected from the group consisting of salicylic acid, acetylsalicylic acid, 5-aminosalicylic acid, diflunisal, ibuprofen, ketoprofen, naproxen, ibufenac, indomethacin, diacerhein and thiorhein and R is a member selected from the group consisting of 5-(2,4-difluorophenyl)-2-hydroxy benzoyl; (4-isobutylphenyl)-acetyl; (4-isobutylphenyl)-propionyl; (6-methoxy-naphthyl)-propionyl; [1-(4-chlorobenzoyl)-2-methyl-5-methoxy-2-indolyl]-acetyl and 2-acetoxybenzoyl.

2. The compound according to claim 1 wherein R is 2-acetoxybenzoyl.

3. The compound according to claim 1, wherein A is —$(CH_2)_5$— or —$(CH_2)_3$—.

4. The method of treatment of osteoarticular and connective tissue disorders in a living subject in need of treatment which consists of administering to said living subject an effective amount of a compound of formula:

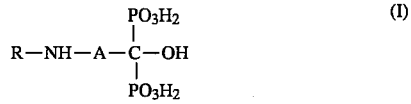

wherein A is —$(CH_2)_5$— or —$(CH_2)_3$— and R is a member selected from the group consisting of 2-acetoxybenzoyl, 5-(2,4-difluorophenyl)-2-hydroxy benzoyl; (4-isobutylphenyl)-acetyl; (4-isobutylphenyl)-propionyl; (6-methoxy-naphthyl)-propionyl and [1-(4-chlorobenzoyl)-2-methyl-5-methoxy-2-indolyl]-acetyl.

5. The method of treatment of osteoarticular and connective tissue disorders in a living subject in need of treatment which consists of administering to said living subject an effective amount of [4-[2-4(4-isobutylphenyl)-propionyl]-amino-1-hydroxybutylidene]diphosphonic acid or [6-[2-(4-isobutylphenyl)-propionyl]-amino-1-hydroxyhexylidene]-diphosphonic acid.

6. A pharmaceutical composition in unit dosage form

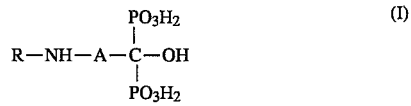

wherein A is $(CH_2)_5$ or —$(CH_2)_3$ and R is a member selected from the group consisting of 2-acetoxybenzoyl, 5-(2,4-difluorophenyl)-2-hydroxy benzoyl; (4-isobutylphenyl)-acetyl; (4-isobutylphenyl)-propionyl; (6-methoxy-naphthyl)-propionyl and [1-(4-chlorobenzoyl)-2-methyl-5-methoxy-2-indolyl]-acetyl. together with excipients.

* * * * *